US008623921B2

(12) United States Patent
Lunsmann et al.

(10) Patent No.: US 8,623,921 B2
(45) Date of Patent: *Jan. 7, 2014

(54) BIS(THIO-HYDRAZIDE AMIDE) FORMULATION

(75) Inventors: Walter J. Lunsmann, Harvard, MA (US); Ninad Deshpanday, Cary, NC (US)

(73) Assignee: Synta Pharmaceuticals Corp., Lexington, MA (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/184,342

(22) Filed: Jul. 15, 2011

(65) Prior Publication Data

US 2011/0294895 A1  Dec. 1, 2011

Related U.S. Application Data

(63) Continuation of application No. 12/697,688, filed on Feb. 1, 2010, now abandoned, which is a continuation of application No. 11/502,590, filed on Aug. 10, 2006, now Pat. No. 7,678,832.

(60) Provisional application No. 60/708,977, filed on Aug. 16, 2005.

(51) Int. Cl.
*A61K 31/16* (2006.01)

(52) U.S. Cl.
USPC .................... 514/599; 514/614; 514/615

(58) Field of Classification Search
USPC ................................ 514/599, 614, 615
See application file for complete search history.

(56) References Cited

U.S. PATENT DOCUMENTS

| 4,012,360 | A | 3/1977 | Schwarzenbach et al. |
| 4,822,777 | A | 4/1989 | Abra |
| 5,840,746 | A | 11/1998 | Ducharme et al. |
| 6,013,836 | A | 1/2000 | Hsu et al. |
| 6,172,108 | B1 | 1/2001 | Vega et al. |
| 6,172,188 | B1 | 1/2001 | Thastrup et al. |
| 6,235,787 | B1 | 5/2001 | Broadhurst et al. |
| 6,365,745 | B1 | 4/2002 | Matsui et al. |
| 6,399,659 | B2 | 6/2002 | Usui et al. |
| 6,435,787 | B1 | 8/2002 | John |
| 6,455,515 | B2 | 9/2002 | Gypser et al. |
| 6,656,971 | B2 | 12/2003 | Wu et al. |
| 6,703,426 | B1 | 3/2004 | Miles et al. |
| 6,762,204 | B2 | 7/2004 | Koya et al. |
| 6,800,660 | B2 | 10/2004 | Koya et al. |
| 6,825,235 | B2 | 11/2004 | Chen et al. |
| 6,924,312 | B2 | 8/2005 | Koya et al. |
| 7,001,923 | B2 | 2/2006 | Koya et al. |
| 7,037,940 | B2 | 5/2006 | Koya et al. |
| 7,074,952 | B2 | 7/2006 | Chen et al. |
| 7,345,094 | B2 | 3/2008 | Koya et al. |
| 7,368,473 | B2 | 5/2008 | Koya et al. |
| 7,385,084 | B2 | 6/2008 | Koya et al. |
| 7,435,843 | B2 | 10/2008 | Chen et al. |
| 7,678,832 | B2 * | 3/2010 | Lunsmann et al. ........... 514/599 |
| 2002/0198160 | A1 | 12/2002 | Everitt et al. |
| 2003/0045518 | A1 | 3/2003 | Koya et al. |
| 2003/0119914 | A1 | 6/2003 | Koya et al. |
| 2004/0022869 | A1 | 2/2004 | Chen et al. |
| 2004/0192900 | A1 | 9/2004 | Kunz et al. |
| 2004/0225016 | A1 | 11/2004 | Koya et al. |
| 2006/0116374 | A1 | 6/2006 | Koya et al. |
| 2006/0122183 | A1 | 6/2006 | Koya et al. |
| 2006/0135595 | A1 | 6/2006 | Koya et al. |
| 2006/0142386 | A1 | 6/2006 | Barsoum |
| 2006/0142393 | A1 | 6/2006 | Sherman et al. |
| 2006/0270873 | A1 | 11/2006 | Chen et al. |
| 2006/0281811 | A1 | 12/2006 | Chen et al. |
| 2007/0088057 | A1 | 4/2007 | Lunsmann et al. |
| 2008/0089950 | A1 | 4/2008 | Chen et al. |
| 2008/0118562 | A1 | 5/2008 | Koya |
| 2008/0119440 | A1 | 5/2008 | Koya |
| 2008/0146842 | A1 | 6/2008 | Chen et al. |

(Continued)

FOREIGN PATENT DOCUMENTS

| DE | 2037257 | 2/1972 |
| FR | 2097737 | 2/1972 |

(Continued)

OTHER PUBLICATIONS

U.S. Appl. No. 12/221,926, filed Aug. 7, 2008.
Al-Talib, M. et al., "Diacyl Acid Dihydrazides," Magnetic Resonance in Chemistry 28:1072-1078 (1990).
Asahi Chemical Ind. KK. Abstract of Japanese Patent No. 50-91056, Accession No. 47521Y/27 (1975).
Barrett, William G. and McKay, Donald, "Decomposition and Cycloaddition Reactions of Some Bis(azodicarbonyl) Compounds," Journal of Chem. Soc. (4):1046-1052 (1975).
Barry, V. C., et al., "Anticancer Agents—III. Synthesis and Anticancer Activity of Some Bis-Thiosemicarbazones and Thoiosemicarbazides," *Proc. R.I.A.* Sect. B(65):309-324 (1967).

(Continued)

*Primary Examiner* — Kevin E Weddington
(74) *Attorney, Agent, or Firm* — McCarter & English, LLP; Steven G. Davis

(57) ABSTRACT

Disclosed herein are compositions comprising a compound represented by structural formula (I):

$$2 M^+ \text{ or } M^{2+}$$

$$R_1 \underset{S}{\overset{R_3}{\underset{\|}{\text{—}}}} \underset{N}{\overset{Z^-}{\underset{\|}{\text{—}}}} \underset{Y}{\overset{Z^-}{\underset{\|}{\text{—}}}} \underset{N}{\overset{R_4}{\underset{\|}{\text{—}}}} R_2,$$

2 g of which is reconstitutable in 10 mL of a water in less than 10 minutes, and methods for preparing these compositions. Also disclosed are compositions comprising a compound represented by structural formula (I) and a pharmaceutically acceptable excipient, wherein the molar ratio of said compound to said excipient is from 1:20 to 1:1, and methods for preparing these compositions.

21 Claims, No Drawings

(56) References Cited

U.S. PATENT DOCUMENTS

| | | |
|---|---|---|
| 2008/0176828 A1 | 7/2008 | Williams et al. |
| 2008/0214655 A1 | 9/2008 | Koya et al. |
| 2008/0226588 A1 | 9/2008 | McLeod |
| 2008/0242702 A1 | 10/2008 | Koya et al. |
| 2008/0269340 A1 | 10/2008 | Koya et al. |
| 2009/0005594 A1 | 1/2009 | Chen et al. |
| 2009/0042991 A1 | 2/2009 | Barsoum et al. |
| 2009/0137682 A1 | 5/2009 | Dahl |

FOREIGN PATENT DOCUMENTS

| | | |
|---|---|---|
| GB | 1 272 920 | 5/1972 |
| JP | 50-91056 | 7/1975 |
| WO | WO 94/10995 A1 | 5/1994 |
| WO | WO 99/34796 A1 | 7/1999 |
| WO | WO 03/006428 A1 | 1/2003 |
| WO | WO 03/006429 A1 | 1/2003 |
| WO | WO 03/006430 A1 | 1/2003 |
| WO | WO 03/047524 A2 | 6/2003 |
| WO | WO 2004/064826 A1 | 8/2004 |
| WO | WO 2006/009940 A1 | 1/2006 |
| WO | WO 2006/033913 A2 | 3/2006 |
| WO | WO 2006/055747 A2 | 5/2006 |
| WO | WO 2006/113493 A2 | 10/2006 |
| WO | WO 2006/113572 A1 | 10/2006 |
| WO | WO 2006/113695 A1 | 10/2006 |
| WO | WO 2006/124736 A2 | 10/2006 |
| WO | WO 2006/124736 A2 | 11/2006 |
| WO | WO 2007/021881 A1 | 2/2007 |
| WO | WO 2008/024298 A1 | 2/2008 |
| WO | WO 2008/024299 A2 | 2/2008 |
| WO | WO 2008/024301 A2 | 2/2008 |
| WO | WO 2008/024302 A2 | 2/2008 |
| WO | WO 2008/024303 A2 | 2/2008 |
| WO | WO 2008/024305 A2 | 2/2008 |
| WO | WO 2008/027445 A2 | 3/2008 |
| WO | WO 2008/033300 A2 | 3/2008 |
| WO | WO 2008/033494 A2 | 3/2008 |
| WO | WO 2009/020631 A2 | 2/2009 |

OTHER PUBLICATIONS

Chuiguk, V.A., and Nemazanyi, A.G., "Mesoionic Methine Dyes of Biquaternary Salts of Diheteroaryl Methanes—Derivatives of 1, 3, 4—oxa (thia) Diazoles and 1, 2, 4—Triazoles," Kiev. Gos. Univ., Kiev, USSR, Ukrainskii Khimicheskii Zhurnal, Russian Edition, 50(5):519-524 (1984). Abstract, Accession No. 1984:630420, HCAPLUS Database.

Chuyguk, V. A. and Nemazanyj A.G., "Mesoionic Methine Dyes from Biquaternary Salts of Dihetarylmethanes—1,3,4-Oxa(thia)diazoles and 1,2,4-Triazoles Derivatives," *Ukr. Khim. Zhurn.* 48:520 (1984). (English Translation).

H. Bräuniger, "Hydrazide and Hydraziddderivate von Dicarbonsäuren," Pharmaceutical-Chemical Institute of University of Rostock, Supplied by the "British Library" 25(5-6) 279-283 (1970).

Honshu Paper Mfg. Co. Ltd, Abstract of Japanese Patent No. 182050, published Feb. 13, 1996.

Merlin, J.L., et al., In Vitro Comparative Evaluation of Trastuzumab (Herceptin®) Combined with Paclitaxel (Taxol®) or Docetaxel (Taxotere®) in HER2-Expressing Human Breast Cancer Cell Lines, *Annals of Oncology* 13:1743-1748 (2002).

Mitsui Toatsu Chem. Inc., Abstract of Japanese Patent No. 308024, published Dec. 25, 1986. from Derwent Publications Ltd.

Molina, P., et al., XP-001118802 "Preparation of a Novel Type of Ligands Incorporating Two or Three 1,3,4-Thiadiazole Units," *Heterocycles* 36(6):1263-1278 (1993).

Molina, P., et al., XP-01118868 "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans.* 1 s 5:1159-1166 (1991).

O'Callaghan, C. N., "Anticancer Agents—X. Cyclisation of 1-Acyl-4-Alkylthiosemicarbazide Derivatives to 1,2,4-Triazoline-3-Thiones in the Presence of Hydrazine," *Proc. R.I.A.*, Sect. B(74):455-461 (1974).

Rupp, Walter, CA76:126992, 1972.

Schwarz et al., CA77:48081, 1972.

Stalteri, M.A., et al., "Site-specific conjugation and labelling of prostate antibody 7E1105.3 (CYT-351) with technetium-99m," *European Journal of Nuclear Medicine* 24(6):651-654, (1997).

Twomey, D., "Anticancer Agents-IX. Derivatives of Pyridine, Pyridazine and Phthalazine," *Proceedings of the Royal Irish Academy*, vol. 74, Sect. B:37-52,(1974).

Goodman & Gilman's, The Pharmacological Basis of Therapeutics, Ninth Edition, (1996), Section X, Calabresi et al., pp. 1225-1232.

Rao et al., "Combination of Paclitaxel and Carboplatin as Second-Line Therapy for Patients with Metastatic Melanoma," *Cancer*, vol. 106, No. 2: 375-382 (Jan. 2006).

Gura et al., "Systems for Identifying New Drugs are Often Faulty," *Science*, 1997, 278: 1041-1042.

Johnson et al., "Relationships Between Drug Activity in NCI Preclinical in vitro and in vivo Models and Early Clinical Trials," *British J. of Cancer*, 2001, 84(10): 1424-1431.

Sausville et al., "Contributions to Human Tumor Xenografts to Anticancer Drug Development," *Cancer Research*, 2006, vol. 66, pp. 3351-3354.

Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.

"The Merck Manual," Chapter 14: Principles of Cancer Therapy, 1999 Merck Research Laboratories, pp. 987-995 (1999), XP002477370.

Wust, P. et al., "Hyperthermia in Combined Treatment of Cancer," *The Lancet Oncology*, 3(8): 487-497 (Aug. 2002), XP004813895.

Biagi, G. et al., "1,5-Diarylsubstituted 1,2,3-triazoles as Potassium Channel Activators. VI," *Il Farmaco*, 59(5): 397-404 (2004), esp. p. 398.

Patinit et al., "Bioisosterism: A Rational Approach in Drug Design," *Chem. Rev.*, 96: 3147-3176 (1996), esp. p. 3152.

Balkwill, F. et al., "Inflammation and Cancer: Back to Virchow?" *The Lancet*, 357: 539-545 (Feb. 2001).

Jacquier-Sarlin, M.R. et al., "Protective Effects of hsp70 in Inflammation," *Experientia*, 50(11-12): 1031-1038 (Nov. 1994).

Cancer, Wikipedia, http://en.wikipedia.org/wiki/Cancer (1 of 40) Aug. 2, 2008 (all pages).

Johnson, R.E. et al., Mannitol-Sucrose Mixtures—Versatile Formulations for Protein Lyophilization, (2002) *Journal of Pharmaceutical Sciences*, 91(4):914-922.

Torrado, S. et al., Characterization of Physical State of Mannitol After Freeze-Drying: Effect of Acetylsalicylic Acid as a Second Crystalline Cosolute, (2002) *Chem. Pharm. Bull.* 50(5):567-570.

Nuijen, B. et al., Development of a lycophilized parenteral pharmaceutical formulation of the investigational polypeptide marine anticancer agent kahalalide F, (2001) *Drug Dev. Ind. Pharm.*, 27(8):767-780 (Abstract).

Fakes et al., Moisture Sorption Behavior of Selected Bulking Agents Used in Lyophilized Products, (2000) *PDA J. Pharm. Sci. and Tech.* 54:144-149.

\* cited by examiner

BIS(THIO-HYDRAZIDE AMIDE) FORMULATION

RELATED APPLICATIONS

This application is a Continuation of U.S. application Ser. No. 12/697,688, filed Feb. 1, 2010, which is a Continuation of U.S. application Ser. No. 11/502,590, filed Aug. 10, 2006, incorporated herein by reference in its entirety, which claims priority from Provisional Application U.S. Application 60/708,977, filed Aug. 16, 2005. The entire teachings of the above application(s) are incorporated herein by reference.

BACKGROUND OF THE INVENTION

Many drugs are now available to be used in the treatment of cancer. However, in many cases the cancer fails to respond to the anti-cancer therapy or its growth and/or metastasis is only slowed. Even when a tumor initially responds to an anti-cancer therapy by decreasing in size or going into remission, the tumor often develops resistance to the drug. For these reasons, there has been a need for new anti-cancer agents and for new drugs which can be used to treat multi-drug resistance cancers.

Certain bis(thio-hydrazide amide) compounds have been described as being significantly cytotoxic to cancer cells, including cancer cells that have become multi-drug resistant, and for enhancing the anti-cancer activity of other anti-cancer agents, such as taxol and taxol analogs (see, e.g., U.S. application Ser. No. 10/758,589, and U.S. Pat. Nos. 6,762,204, and 6,800,660, the entire contents of which are incorporated herein by reference).

These bis(thio-hydrazide amide) are themselves only marginally soluble in water. However, their disalts (as disclosed in U.S. application Ser. No. 11/157,213, the entire contents of which are incorporated herein by reference) show high water solubility and bioavailability. Typically these disalts suffer from long reconstitution times in water, and due to a low glass transition temperature these disalts require specialized lyophilization equipment which increases costs associated with drying these disalts.

Therefore, a need exists for methods which decrease costs associated with drying these disalts and which shorten the reconstitution times of the disalts.

SUMMARY OF THE INVENTION

It has now been found that reconstitution times for certain bis(thio-hydrazide amide) disalts can be decreased considerably by lyophilizing and annealing the disalts in the presence of a crystalline bulking excipient under certain conditions. It has also been found that by lyophilizing and annealing these disalts in the presence of a crystalline bulking excipient, specialized lyophilized equipment is not required, and therefore manufacturing costs are considerably reduced.

In one embodiment, the present invention relates to a composition comprising a compound represented by structural formula (I):

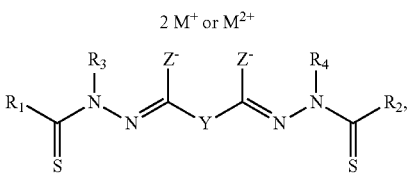

Y is a covalent bond or a substituted or unsubstituted straight chained hydrocarbyl group.

$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

Z is —O or —S.

$M^+$ is a pharmaceutically acceptable monovalent cation and $M^{2+}$ is a pharmaceutically acceptable divalent cation.

2 g of the composition comprising a compound represented by structural formula (I) is reconstitutable in 10 mL of a water in less than 10 minutes.

In another embodiment, the present invention relates to a composition comprising a compound represented by structural formula (I) and a pharmaceutically acceptable excipient, wherein the molar ratio of said compound to said excipient is from 1:20 to 1:1.

In another embodiment, the present invention relates to a method for preparing a lyophilizate of a composition comprising a compound represented by structural formula (I) and a pharmaceutically acceptable crystalline bulking excipient. The method comprises the steps of:

a) preparing an aqueous solution of the compound and the excipient wherein the molar ratio of said compound to said excipient is from 1:20 to 1:1;

b) freezing the solution of step a) at a temperature below the glass transition temperature of the compound to form a freeze-concentrate;

c) annealing the freeze-concentrate at a temperature above the glass transition temperature of the compound but below the melting temperature of the frozen solution comprising the freeze-concentrate, to form an annealed composition;

d) freezing the annealed composition at a temperature below the glass transition temperature of the compound; and e) drying the annealed composition of step e) to obtain a lyophilizate with a moisture content of less than 10%.

In another embodiment, the present invention relates to a lyophilizate comprising a compound represented by structural formula (I) and a pharmaceutically acceptable crystalline bulking excipient. The lyophilizate is prepared by the process described immediately above:

In another embodiment, the present invention relates to a method for preparing a lyophilizate of a composition comprising a compound represented by structural formula (I) and a pharmaceutically acceptable excipient, selected from the group hydroxyethyl starch, dextran and combinations thereof. The method comprises the steps of:

a) preparing an aqueous solution of the compound and the excipient;

b) freezing the solution of step a) at a temperature below the glass transition temperature of the compound to form a freeze-concentrate; and c) drying said freeze-concentrate to obtain a lyophilizate with a moisture content of less than 10%.

In another embodiment, the present invention relates to a lyophilizate comprising a compound represented by structural formula (I) and a pharmaceutically acceptable excipient, selected from the group hydroxyethyl starch, dextran and combinations thereof. The lyophilizate is prepared by the process described immediately above.

In another embodiment, the present invention relates to the use of the compositions, disclosed herein in therapy, for example, as anti-cancer agents.

The present invention also provides for a method of treating a subject with a cancer. The method comprises administering to the subject an effective amount of a composition disclosed herein. The composition is administered as a monotherapy (i.e., as the only anti-cancer drug administered to the subject) or is co-administered with one or more other anti-cancer drugs.

In another embodiment the present invention relates to the use of composition or lyophilizate disclosed herein in the manufacture of a medicament for the purpose of treating cancer in an individual.

The disclosed methods allow for the lyophilized (and optionally annealed) compositions disclosed herein to be dried and stored for long periods of time without deterioration of the compositions. Also, the high water solubility of the lyophilized (and optionally annealed) compositions disclosed herein allows for fast reconstitution of the composition without the need for specialized equipment such as sonic baths etc. The lyophilization and annealing process described herein are also conducted under standard conditions without the need for high vacuum and low temperatures typically require for compounds with low glass transition temperatures, which would greatly increase the costs associated the lyophilization procedure.

DETAILED DESCRIPTION OF THE INVENTION

The present invention relates to compositions comprising a bis(thio-hydrazide amide) compound which is a compound whose structure is encompassed by a formula selected from Structural Formulas (I)-(V), as described below, 2 g of which is reconstitutable in 10 mL in less than 10 minutes; preferably in less than 5 minutes, more preferably less than 2 minutes, even more preferably less than 1 minute, still more preferably, less than 30 seconds.

The terms "reconstitutable" or "reconstituted" as defined herein means that the composition or annealed composition and/or lyophilized composition of the present invention can be dissolved completely in water under ambient conditions.

In a preferred embodiment, the composition further comprises a pharmaceutically acceptable excipient. The term "pharmaceutically acceptable excipient" as used herein refers to a substance which is added to a solution prior to lyophilization to enhance characteristics such as the color, texture, strength, and volume of the lyophilized cake. Pharmaceutically acceptable excipients may be, for example, buffers and pH adjusters, crystalline bulking excipients, stabilizers, and tonicity raising agents.

In certain preferred embodiments the pharmaceutically acceptable excipient is a crystalline bulking excipient. The terms "crystalline bulking excipient" or "crystalline bulking agent" as used herein means an excipient which provides bulk and structure to the lyophilization cake. These crystalline bulking agents are inert and do not react with the bis(thio-hydrazide amide). In addition, the crystalline bulking agents are capable of crystallizing under lyophilization conditions. The crystalline bulking agent may form a crystal structure combined with the bis(thio-hydrazide amide), or may form a crystal structure independent of the bis(thio-hydrazide amide).

Examples of suitable crystalline bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, glucose, fructose, gulose, idose, galactose, talose, ribose, arabinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats and polyvinylpyrrolidone.

Preferred crystalline bulking agents are selected from the group consisting of glycine, mannitol, dextran, dextrose, lactose, sucrose, polyvinylpyrrolidone, trehalose, glucose and combinations thereof. Other preferred crystalline bulking agent are glycine or mannitol. In certain other preferred embodiments, the crystalline bulking agent is mannitol.

In certain embodiments the crystalline bulking agents is present in a molar ratio of bis(thio-hydrazide amides) relative to the excipient of 1:20 to 1:1, preferably 1:10 to 1:1. Typically, the excipients are present in a molar ratio excess of the bis(thio-hydrazide amide) disalt to the excipients of, for example, from, 1:20 to 1:2, preferably from 1:10 to 1:2, even more preferably from 1:5.5 to 1:2.0.

In other embodiments, a pharmaceutically acceptable excipient can be used in combination with the bis(thio-hydrazide amide) wherein the pharmaceutically acceptable excipient forms a gelatin or polymer structure which can be amorphous or crystalline. Examples of such pharmaceutically acceptable excipients include hydroxyethyl starch, dextran, polyvinylpyrrolidone, gelatin, pullan, starch, pectin, amylopectin, chitin and combinations thereof, preferably the excipient is selected from hydroxyethyl starch, dextran and combinations thereof. Typically these excipient are present in a weight ratio of the bis(thio-hydrazide amide) to the excipient of from 1:0.5 to 1:20 preferably from 1:1 to 1:10, more preferably from 1:1 to 1:5, even more preferably from 1:1 to 1:2.

For one embodiment, the composition comprising the bis (thio-hydrazide amide), and a pharmaceutically acceptable excipient, is a lyophilized, more preferably a lyophilized and annealed composition. Alternatively, the disclosed compositions are lyophilized or unlyophilized. When unlyophilized these compositions can be starting materials used to prepare the lyophilized and annealed compositions of the invention by means of the processes described below.

The term "lyophilization" as used herein is a freeze drying or dehydration technique which involves removing a solvent, preferably a water miscible solvent, more preferably water from a composition, typically by sublimation under high vacuum when the composition is in a frozen state. Lyophilization stabilizes the composition and minimizes oxidation and other degradative processes allowing for long term storage of the composition at temperatures above freezing.

The terms "lyophilized composition", "lyophilized cake" or "lyophilizate" as used herein mean the solid residue or cake which is produced or which remains after the lyophilization procedure as defined above. In certain embodiments, the lyophilized formulation or lyophilizate has a moisture content of less than 10%, preferably less than 5%, more preferably less than 2%, even more preferably less than 1%. The final moisture of a lyophilized formulation, can be measured by Karl Fisher or other methods.

Typically, lyophilization is carried out in lyophilization equipment (a lyophillizer), which comprises a drying chamber with variable temperature controls, a condenser to collect water, and a vacuum system to reduce the pressure in the drying chamber.

The lyophilization process generally includes two steps: a freezing step and a primary drying or sublimation step, and can optionally include a secondary drying step. The lyophilization process may also include a pretreatment stage, carried out prior to the freezing stage and an annealing stage carried out during prior to the drying stage.

As used herein "pretreatment" includes any method of treating the composition or solution prior to freezing. This may include, for example, concentrating the solution, formulation revision (i.e., addition of components to increase stability and/or improve processing), or pre-cooling the solution.

In certain preferred embodiments the composition or solution is precooled at between 10° C. and −10° C., preferably, between 0° C. and −10° C., over a time period of between 10 seconds and 1 hour, preferably between 1 minute and 30 minutes.

To prepare the disclosed reconstitutable compositions, a bis(thiohydrazide amide) and a pharmaceutically acceptable excipient is dissolved or suspended in a suitable solvent, preferably the bis(thio-hydrazide amide) and the pharmaceutically acceptable excipient are dissolved in a suitable solvent to form a solution. Typically, the solvent is an aqueous solvent and can optionally comprise other ingredients such as buffers, pharmaceutically acceptable salts or other pharmaceutically acceptable ingredients dissolved therein. Typically, the solvent is sterile water with no other ingredients. Alternatively, the solvent is a non-aqueous solvent, such as, an alcohol, e.g., methanol, ethanol, tert-butyl alcohol or a water/alcohol mixture, dimethylsulfoxide (DMSO), tetrahydrafuran (THF), or dimethylformamide (DMF).

The first stage of the disclosed lyophilization process, after any pre-treatment steps, is freezing. In the freezing step, the solution is frozen at a temperature below the glass transition temperature of the bis(thio-hydrazide amide) to form a freeze-concentrate.

Glass transition temperature (Tg), as defined herein is the temperature at which a compound changes state from that of a glassy rigid state to that of a viscous liquid. For example, below the Tg materials are typically rigid or glassy, and typically are rubbery or leathery above the Tg. The glass transition is not always a sharp transition and in certain instances can be a gradual transition. For the bis(thio-hydrazide amide of Structural Formula, (II) the Tg is −44.7° C.

As the solution freezes the concentration of the compound and excipient increases in solution, Tg' is the glass transition temperature at the maximum concentration of drug and excipient in solution.

Freezing produces a "freeze concentrate" of a highly concentrated, composition or mixture consisting of the compound of the present invention and excipient or excipients interlaced in the interstitial region of the ice crystals.

In certain preferred embodiments, in the freeing step the solution is frozen at a temperature between −44.7° C. and −80° C., preferably, between −44.7° C. and −60° C., preferably between −44.7° C. and −50° C., over a time period of between 10 minutes and 10 hours, preferably between 30 minutes and 3 hours, more preferably, between 30 minutes and 2 hours.

In the next step of the disclosed lyophilization procedure, the "freeze-concentrate" is optionally annealed. The terms "annealed" or "annealing" as used herein is a process of holding the temperature of the freeze-concentrate at a constant temperature for a duration of time that allows the crystalline bulking excipient to crystallize. Typically, the freeze-concentrate is annealed at a temperature between the melting point of the frozen solution comprising the freeze-concentrate, and the Tg of the compound of the present invention. The melting point of the frozen solution comprising the freeze-concentrate as used herein is the temperature at which the frozen solution comprising the bis(thio-hydrazide amide) and excipient changes from a solid frozen state to a liquid state or starts to melt. Typically this temperature is around 0° C. but will vary depending on the concentration of the solution. When the freeze-concentrate of the present invention are annealed, the crystalline bulking excipient forms a crystal structure independent of the compound of the present invention.

In certain preferred embodiments, the annealing step is carried out once. In certain more preferred embodiment, the annealing step is carried out more than once, such as twice, three times, five times or ten times. Typically, the annealing step is carried out twice.

In certain preferred embodiments, in the annealing step the freeze-concentrate is annealed at a temperature between 0° C. and −44.7° C., preferably, between 0° C. and −40° C. and, preferably between 0° C. and −30° C. over a time period of between 10 minutes and 10 hours, preferably between 2 hours and 6 hours, more preferably, between 3 hours and 5 hours.

The term "annealed composition" as used herein is any composition which has been annealed as defined above.

In the next step in the disclosed lyophilization procedure, the annealed composition can be frozen to a temperature below the Tg of the bis(thio-hydrazide amide). In this freeing step, the solution is frozen at a temperature between −44.7° C. and −80° C., preferably, between −44.7° C. and −60° C., preferably between 44.7° C. and −50° C. over a time period of between 10 minutes and 10 hours, preferably between 30 minutes and 3 hours, more preferably, between 30 minutes and 1.5 hours.

The term "drying" as used herein encompasses any method of removing water or solvent from the freeze-concentrate or annealed composition while maintaining the glassy state of the freeze-concentrate or annealed composition.

The primary drying step involves the sublimation of the aqueous solution or solvent components under a vacuum at temperatures low enough to prevent collapse of the freeze-concentrate. In certain particular embodiments, the aqueous or solvent components are removed by sublimation during primary drying. The temperature of the drying step must be high enough to provide a sufficient rate of sublimation of the liquid components yet low enough to insure that all components of the freeze-concentrate remain frozen. Since sublimation provides considerable cooling to the product, temperatures for the drying step are generally much higher than those for the freezing step.

In the primary drying step the freeze-concentrate or annealed composition is dried by sublimation at a temperature between 20° C. and −20° C., preferably, between 10° C. and −10° C., preferably between 10° C. and 0° C. additional sublimation temperatures include between 0° C. and −30° C., preferably between 0° C. and −25° C. Typically sublimation is carried out under vacuum conditions at pressures of between 200 mTorr and 20 mTorr, preferably between 200 mTorr and 100 mTorr, more preferable, between 180 mTorr and 130 mTorr.

Sublimation is carried out over a time period of between 5 hours and 40 hours, preferably between 10 hours and 30 hours, more preferably, between 20 hours and 30 hours, additionally sublimation is carried out over a time period of between 10 hours and 80 hours, preferably between 30 hours and 60 hours.

After removal of the ice crystals by sublimation, the remaining freeze-concentrate or annealed composition may still contain bound water/solvent that may be removed by slow heating which is optionally conducted under vacuum conditions to produce the lyophilized cake. This is the final segment of the lyophilization cycle where residual moisture is reduced to levels that no longer support biological growth and chemical reaction. This process is secondary drying. The reduction of moisture in during secondary drying is accomplished by increasing the temperature to ambient temperature or above.

In the secondary drying step the freeze-concentrate or annealed composition is dried by desorption at a temperature between 20° C. and 80° C., preferably, between 30° C. and 60° C., preferably between 40° C. and 50° C. additional desorption temperatures include 10° C. to 80, preferably, 10° C. to 30° C. Typically desorption is carried out under vacuum conditions at pressures of between 200 mTorr and 20 mTorr, preferably between 200 mTorr and 100 mTorr, more preferable, between 180 mTorr and 130 mTorr.

In a particular embodiment, desorption is carried out over a time period of between 10 minutes and 10 hours, preferably between 30 minutes and 5 hours, more preferably, between 1 hour and 3 hours, additional desorption times include 10 to 30 hours, preferably 10 to 20 hours.

The lyophilized formulation or lyophilizate is typically dried until it has a moisture content of less than 10%, preferably less than 5%, more preferably less than 2%, even more preferably less than 1%. The final moisture of a lyophilized formulation, can be measured by Karl Fisher or other methods.

Typical lyophilization cycle useful in accordance with the present invention are provided below. The cycles may be varied depending upon the equipment and facilities available in a manner well known in the art.

In one embodiment, the lyophilized composition is prepared by the following procedure. The temperature of the chamber is optionally reduced to between 10° C. and −10° C. and maintained for a period of between 5 minutes and 5 hours prior to freezing. The temperature of the chamber is then reduced to between −44.7° C. and −80° C. and the temperature is maintained for between 10 minutes and 10 hours. The temperature is then increased to between 0° C.-44.7° C. and held for between 10 minutes and 10 hours. The temperature of the chamber is then reduced to between −44.7° C. and −80° C. and the temperature is maintained for between 10 minutes and 10 hours. The temperature is then optionally increased to between 0° C. and −44.7° C. and held for between 10 minutes and 10 hours. The temperature of the chamber is then reduced to between −44.7° C. and −80° C. and the temperature is maintained for between 10 minutes and 10 hours. The pressure in the lyophilization chamber is then reduced to between 20 mTorr and 200 mTorr. After reducing the pressure in the chamber, the temperature is ramped up to between 20° C. and −20° C. and maintained for between 4 and 40 hours. The temperature then is optionally ramped up to between 20° C. and 80° C. and held for between 10 minutes and 10 hours. The lyophilized product preferably has a final moisture content of between less than about 10% and less than about 1%, typically about 1%.

In an additionally embodiment, the lyophilized composition is prepared by the following procedure. The temperature of the chamber is optionally reduced to between 10° C. and 0° C. and maintained for a period of between 5 minutes and 1 hour prior to freezing. The temperature of the chamber is then reduced to between −44.7° C. and −60° C. and the temperature is maintained for between 30 minutes and 3 hours. The temperature is then increased to between 0° C. and −40° C. and held for between 2 hours and 6 hours. The temperature of the chamber is then reduced to between −44.7° C. and −60° C. and the temperature is maintained for between 30 minutes and 3 hours. The temperature in then optionally increased to between 0° C.-40° C. and held for between 2 hours and 6 hours. The temperature of the chamber is then reduced to between −44.7° C. and −60° C. and the temperature is maintained for between 30 minutes and 3 hours. The pressure in the lyophilization chamber is then reduced to between 100 mTorr and 200 mTorr. After reducing the pressure in the chamber, the temperature is ramped up to between 10° C. and −10° C. and maintained for between 20 and 30 hours. The temperature then is optionally ramped up to between 30° C. and 60° C. and held for between 1 hour and 3 hours. The lyophilized product preferably has a final moisture content of between less than about 10% and less than about 1%, typically about 1%.

In another additional embodiment, the lyophilized composition is prepared by the following procedure. The temperature of the chamber is optionally reduced to −5° C. and maintained for a period of 15 minutes. The temperature of the chamber is then reduced to −48° C. and the temperature is maintained for about 1 hour. The temperature in then increased to −20° C. and held for about 4 hours. The temperature of the chamber is then reduced to −48° C. and the temperature is maintained for about 1 hour. The temperature in then optionally increased to −20° C. and held for about 3 hours. The temperature of the chamber is then reduced to −48° C. and the temperature is maintained for about 1 hour. The pressure in the lyophilization chamber is then reduced to 100-200 mTorr. After reducing the pressure in the chamber, the temperature is ramped up to +5° C. and maintained for about 25 hours. The temperature then is optionally ramped up to +45° C. over a and held for 3 hours. The lyophilized product preferably has a final moisture content of less than about 2% and typically about 1%.

In yet another additional embodiment, the lyophilized composition is prepared by the following procedure. The temperature of the chamber is optionally reduced to between 10° C. and 0° C. and maintained for a period of between 5 minutes and 1 hour. The temperature of the chamber is then reduced to between −44.7° C. and −60° C. and the temperature is maintained for between 30 minutes and 3 hours. The pressure in the lyophilization chamber is then reduced to between 100 mTorr and 200 mTorr. After reducing the pressure in the chamber, the temperature is ramped up to between 0° C. and −30° C. and maintained for between 30 and 60 hours. The temperature then is optionally ramped up to between 10° C. and 30° C. and held for between 10 hours and 30 hours. The lyophilized product preferably has a final moisture content of between less than about 10% and less than about 1%, typically about 1%.

Another embodiment of the present invention is a pharmaceutical composition comprising a lyophilized, reconstituted bis(thio-hydrazide amide) as disclosed herein and a pharmaceutically acceptable carrier or diluent.

For the bis(thio-hydrazide amides) described herein of Structural Formula (I)-(V), $M^+$ is a pharmaceutically acceptable monovalent cation. $M^{2+}$ is a pharmaceutically acceptable divalent cation. "Pharmaceutically acceptable" means that the cation is suitable for administration to a subject. Examples of $M^+$ or $M^{2+}$ include $Li^+$, $Na^+$, $K^+$, $Mg^{2+}$, $Ca^{2+}$, $Zn^{2+}$, and $NR_4^+$, wherein each R is independently hydrogen, a substituted or unsubstituted aliphatic group (e.g., a hydroxyalkyl group, aminoalkyl group or ammoniumalkyl group) or substituted or unsubstituted aryl group, or two R groups, taken together, form a substituted or unsubstituted non-aromatic heterocyclic ring optionally fused to an aromatic ring. Preferably, the pharmaceutically acceptable cation is $Li^+$, $Na^+$, $K^+$, $NH_3(C_2H_5OH)^+$, $N(CH_3)_3(C_2H_5OH)^+$, arginine or lysine. More preferably, the pharmaceutically acceptable cation is $Na^+$ or $K^+$. $Na^+$ is even more preferred.

In Structural Formula (I), Z is preferably —O. More preferably, Z is —O; $R_1$ and $R_2$ are the same; and $R_3$ and $R_4$ are the same.

In one embodiment, Y in Structural Formula (I) is a covalent bond, —C($R_5R_6$)—, —($CH_2CH_2$)—, trans-(CH═CH)—, cis-(CH═CH)— or —(CC)— group, preferably —C($R_5R_6$)—. $R_1$-$R_4$ are as described above for Structural Formula (I). $R_5$ and $R_6$ are each independently —H, an aliphatic or substituted aliphatic group, or $R_5$ is —H and $R_6$ is a substituted or unsubstituted aryl group, or, $R_5$ and $R_6$, taken together, are a C2-C6 substituted or unsubstituted alkylene group. The pharmaceutically acceptable cation is as described above.

In one embodiment the bis(thio-hydrazide amides) described herein are represented by Structural Formula (III):

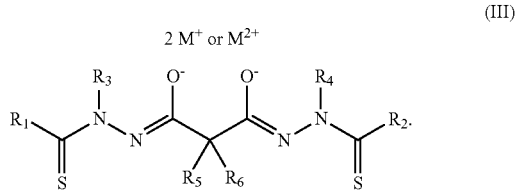

(III)

$R_1$-$R_6$ and the pharmaceutically acceptable cation are as described above for Structural Formula (I).

In another embodiment, the bis(thio-hydrazide amide) is represented by Structural Formula (III) where $R_1$ and $R_2$ are each a substituted or unsubstituted aryl group, preferably a substituted or unsubstituted phenyl group; $R_3$ and $R_4$ are each a substituted or unsubstituted aliphatic group, preferably an alkyl group, more preferably, methyl or ethyl; and $R_5$ and $R_6$ are as described above, but $R_5$ is preferably —H and $R_6$ is preferably —H, an aliphatic or substituted aliphatic group.

Additionally, $R_1$ and $R_2$ are each a substituted or unsubstituted aryl group; $R_3$ and $R_4$ are each a substituted or unsubstituted aliphatic group; $R_5$ is —H; and $R_6$ is —H, an aliphatic or substituted aliphatic group. Preferably, $R_1$ and $R_2$ are each a substituted or unsubstituted aryl group; $R_3$ and $R_4$ are each an alkyl group; and $R_5$ is —H and $R_6$ is —H or methyl. Even more preferably, $R_1$ and $R_2$ are each a substituted or unsubstituted phenyl group; $R_3$ and $R_4$ are each methyl or ethyl; and $R_5$ is —H and $R_6$ is —H or methyl. Suitable substituents for an aryl group represented by $R_1$ and $R_2$ and an aliphatic group represented by $R_3$, $R_4$ and $R_6$ are as described below for aryl and aliphatic groups.

In another embodiment, the bis(thio-hydrazide amide) disalt is represented by Structural Formula (III) where $R_1$ and $R_2$ are each a substituted or unsubstituted aliphatic group, preferably a C3-C8 cycloalkyl group optionally substituted with at least one alkyl group, more preferably cyclopropyl or 1-methylcyclopropyl; $R_3$ and $R_4$ are as described above for Structural Formula (I), preferably both a substituted or unsubstituted alkyl group; and $R_5$ and $R_6$ are as described above, but $R_5$ is preferably —H and $R_6$ is preferably —H, an aliphatic or substituted aliphatic group, more preferably —H or methyl.

Additionally, the bis(thio-hydrazide amide) disalt is represented by Structural Formula (III) where $R_1$ and $R_2$ are each a substituted or unsubstituted aliphatic group; $R_3$ and $R_4$ are as described above for Structural Formula (I), preferably both a substituted or unsubstituted alkyl group; and $R_5$ is —H and $R_6$ is —H or an optionally substituted aliphatic group. Preferably, $R_1$ and $R_2$ are both a C3-C8 cycloalkyl group optionally substituted with at least one alkyl group; $R_3$ and $R_4$ are both as described above for Structural Formula (I), preferably an alkyl group; and $R_5$ is —H and $R_6$ is —H or an aliphatic or substituted aliphatic group. More preferably, $R_1$ and $R_2$ are both a C3-C8 cycloalkyl group optionally substituted with at least one alkyl group; $R_3$ and $R_4$ are both an alkyl group; and $R_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl; and $R_5$ is —H and $R_6$ is —H or methyl.

The following are specific examples of bis(thio-hydrazide amide) disalts represented by Structural Formula (III): $R_1$ and $R_2$ are both phenyl; $R_3$ and $R_4$ are both methyl; $R_5$ is —H, and $R_6$ is ethyl; $R_1$ and $R_2$ are both phenyl; $R_3$ and $R_4$ are both phenyl, and $R_5$ and $R_6$ are both methyl; $R_1$ and $R_2$ are both 2-thienyl; $R_3$ and $R_4$ are both phenyl, and $R_5$ and $R_6$ are both methyl; $R_1$ and $R_2$ are both 4-cyanophenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is benzyl; $R_1$ and $R_2$ are both phenyl; $R_3$ and $R_4$ are both methyl; $R_5$ is —H, and $R_6$ is ethyl; $R_1$ and $R_2$ are both phenyl; $R_3$ and $R_4$ are both ethyl; $R_5$ is —H, and $R_6$ is n-butyl; $R_1$ and $R_2$ are both 2,5-dimethoxyphenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is iso-propyl; $R_1$ and $R_2$ are both 3-nitrophenyl; $R_3$ and $R_4$ are both methyl; $R_5$ is —H, and $R_6$ is methyl; $R_1$ and $R_2$ are both 4-chlorophenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is 3-thienyl; $R_1$ and $R_2$ are both phenyl; $R_3$ and $R_4$ are both methyl, and $R_5$ and $R_6$, taken together, are propylene; $R_1$ and $R_2$ are both 2,3-dimethoxyphenyl; $R_3$ and $R_4$ are both methyl; $R_5$ is —H, and $R_6$ is methyl; $R_1$ and $R_2$ are both 2-chloro-5-methoxy phenyl; $R_3$ and $R_4$ are both methyl; $R_5$ is —H, and $R_6$ is methyl; $R_1$ and $R_2$ are both 2,5-difluorophenyl; $R_3$ and $R_4$ are both methyl; $R_5$ is —H, and $R_6$ is methyl; $R_1$ and $R_2$ are both 2,5-dichlorophenyl; $R_3$ and $R_4$ are both methyl; $R_5$ is —H, and $R_6$ is methyl; $R_1$ and $R_2$ are both 2,6-dimethoxyphenyl; $R_3$ and $R_4$ are both methyl; $R_5$ is —H, and $R_6$ is methyl; $R_1$ and $R_2$ are both 2,5-dimethylphenyl; $R_3$ and $R_4$ are both methyl; $R_5$ is —H, and $R_6$ is methyl; $R_1$ and $R_2$ are both 2,5-dimethoxyphenyl; $R_3$ and $R_4$ are both ethyl; $R_5$ is —H, and $R_6$ is methyl, and $R_1$ and $R_2$ are both 2,5-diethoxyphenyl; $R_3$ and $R_4$ are both methyl; $R_5$ is —H, and $R_6$ is methyl; $R_1$ and $R_2$ are both cyclopropyl; $R_3$ and $R_4$ are both methyl; $R_5$ and $R_6$ are both —H; $R_1$ and $R_2$ are both cyclopropyl; $R_3$ and $R_4$ are both ethyl; $R_5$ and $R_6$ are both —H; $R_1$ and $R_2$ are both cyclopropyl; $R_3$ and $R_4$ are both methyl; $R_5$ is methyl; $R_6$ is —H; $R_1$ and $R_2$ are both 1-methylcyclopropyl; $R_3$ and $R_4$ are both methyl; $R_5$ and $R_6$ are both —H; $R_1$ and $R_2$ are both 1-methylcyclopropyl; $R_3$ and $R_4$ are both methyl; $R_5$ is methyl and $R_6$ is —H; $R_1$ and $R_2$ are both 1-methylcyclopropyl; $R_3$ and $R_4$ are both methyl; $R_5$ is ethyl and $R_6$ is —H; $R_1$ and $R_2$ are both 1-methylcyclopropyl; $R_3$ and $R_4$ are both methyl; $R_5$ is n-propyl and $R_6$ is —H; $R_1$ and $R_2$ are both 1-methylcyclopropyl; $R_3$ and $R_4$ are both methyl; $R_5$ and $R_6$ are both methyl; $R_1$ and $R_2$ are both 1-methylcyclopropyl; $R_3$ and $R_4$ are both ethyl; $R_5$ and $R_6$ are both —H; $R_1$ and $R_2$ are both 1-methylcyclopropyl; $R_3$ is methyl, and $R_4$ is ethyl; $R_5$ and $R_6$ are both —H; $R_1$ and $R_2$ are both 2-methylcyclopropyl; $R_3$ and $R_4$ are both methyl; $R_5$ and $R_6$ are both —H; $R_1$ and $R_2$ are both 2-phenylcyclopropyl; $R_3$ and $R_4$ are both methyl; $R_5$ and $R_6$ are both —H; $R_1$ and $R_2$ are both 1-phenylcyclopropyl; $R_3$ and $R_4$ are both methyl; $R_5$ and $R_6$ are both —H; $R_1$ and $R_2$ are both cyclobutyl; $R_3$ and $R_4$ are both methyl; $R_5$ and $R_6$ are both —H; $R_1$ and $R_2$ are both cyclopentyl; $R_3$ and $R_4$ are both methyl; $R_5$ and $R_6$ are both —H; $R_1$ and $R_2$ are both cyclohexyl; $R_3$ and $R_4$ are both methyl; $R_5$ and $R_6$ are both —H; $R_1$ and $R_2$ are both cyclohexyl; $R_3$ and $R_4$ are both phenyl; $R_5$ and $R_6$ are both —H; $R_1$ and $R_2$ are both methyl; $R_3$ and $R_4$ are both methyl; $R_5$ and $R_6$ are both —H; $R_1$ and $R_2$ are both methyl; $R_3$ and $R_4$ are both t-butyl; $R_5$ and $R_6$ are both —H; $R_1$ and $R_2$ are both methyl; $R_3$ and $R_4$ are both phenyl; $R_5$ and $R_6$ are both —H; $R_1$ and $R_2$ are both t-butyl; $R_3$ and $R_4$ are both methyl; $R_5$ and $R_6$ are both —H; $R_1$ and $R_2$ are both ethyl; $R_3$ and $R_4$ are both methyl; $R_5$ and $R_6$ are both —H; $R_1$ and $R_2$ are both n-propyl; $R_3$ and $R_4$ are both methyl; $R_5$ and $R_6$ are both —H. In these examples, the pharmaceutically acceptable cation represented by $M^+$ and $M^{2+}$ is as described for Structural Formula (I), preferably $Li^+$, $Na^+$, $K^+$, $NH_3(C_2H_5OH)^+$ or $N(CH_3)_3(C_2H_5OH)^+$, more preferably $Na^+$ or $K^+$, even more preferably $Na^+$.

For many bis(thio-hydrazide amide) disalts represented by Structural Formula (III), $R_5$ and $R_6$ are both —H. Examples include wherein: $R_1$ and $R_2$ are both phenyl, and $R_3$ and $R_4$ are both o-$CH_3$-phenyl; $R_1$ and $R_2$ are both o-$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-$CF_3$-phenyl; $R_1$ and $R_2$ are both methyl, and $R_3$ and $R_4$ are both o-$CH_3$-phenyl; $R_1$ and $R_2$ are both —$(CH_2)_3$COOH; and $R_3$ and $R_4$ are both phenyl; $R_1$ and $R_2$ are both represented by the following structural formula:

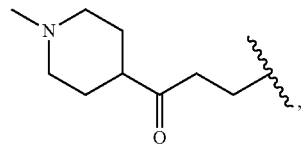 [SMILES: *CCC(=O)C1CCN(C)CC1]

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl. In these examples, the pharmaceutically acceptable cation represented by $M^+$ and $M^{2+}$ is as described for Structural Formula (I), preferably $Li^+$, $Na^+$, $K^+$, $NH_3(C_2H_5OH)^+$ or $N(CH_3)_3(C_2H_5OH)^+$, more preferably $Na^+$ or $K^+$, even more preferably $Na^+$.

Preferred examples of bis(thio-hydrazide amide) disalts, for use in the present invention, are represented by the following structural formulas:

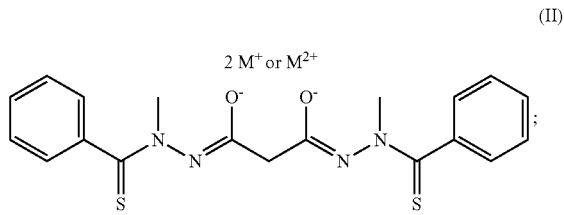

(II)

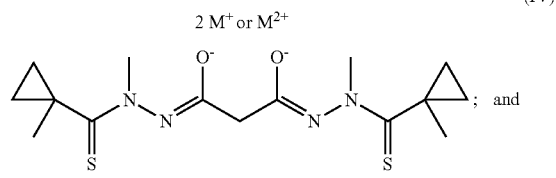

(IV); and

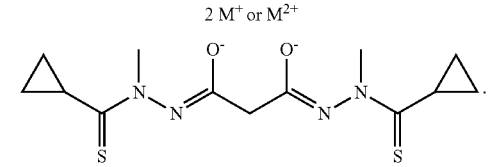

(V)

$2M^+$ and $M^{2+}$ are as described above for Structural Formula (I). Preferably, the pharmaceutically acceptable cation is $2M^+$, wherein $M^+$ is $Li^+$, $Na^+$, $K^+$, $NH_3(C_2H_5OH)^+$ or $N(CH_3)_3(C_2H_5OH)^+$. More preferably, $M^+$ is $Na^+$ or K. Even more preferably, $M^+$ is $Na^+$.

In Structural Formulas (I) and (III), $R_1$ and $R_2$ are the same or different and/or $R_3$ and $R_4$ are the same or different. Preferably, $R_1$ and $R_2$ are the same and $R_3$ and $R_4$ are the same.

The disclosed bis(thio-hydrazide amide) disalts may have tautomeric forms. By way of example, tautomeric forms of the compounds represented by, for example, Structural Formula (I) wherein Y is —$CH_2$— are shown below:

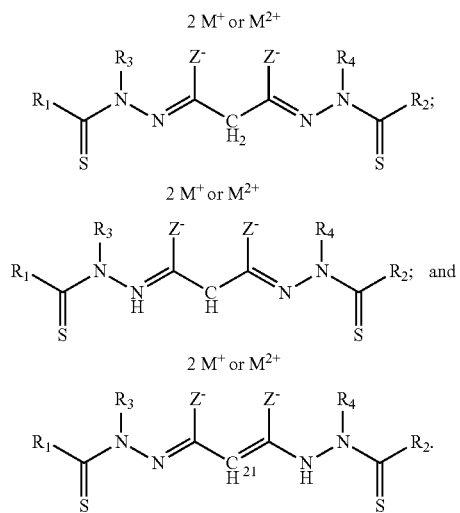

It is to be understood when one tautomeric form of a disclosed compound is depicted structurally, other tautomeric forms are also encompassed.

A "straight chained hydrocarbyl group" is an alkylene group, i.e., —$(CH_2)_y$—, with one or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N($R^a$)—), wherein $R^a$ is defined below. A preferred linkage group is —C($R_5R_6$)—, wherein $R_5$ and $R_6$ are defined above. Suitable substituents for an alkylene group and a hydrocarbyl group are those which do not substantially interfere with the anti-cancer activity of the disclosed compounds. $R_5$ and $R_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g. methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." Heteroaryl groups are aromatic groups that comprise one or more heteroatom, such as sulfur, oxygen and nitrogen, in the ring structure. Preferably, heteroaryl groups comprise from one to four heteroatoms.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

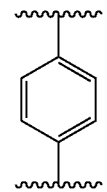 [SMILES: *c1ccc(*)cc1]

Substituents for an arylene group are as described below for an aryl group.

Non-aromatic heterocyclic rings are non-aromatic rings which include one or more heteroatoms such as nitrogen, oxygen or sulfur in the ring. The ring can be five, six, seven or eight-membered. Preferably, heterocyclic groups comprise from one to about four heteroatoms. Examples include tetrahydrofuranyl, tetrahyrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the disclosed compounds. A substituent substantially interferes with anti-cancer activity when the anti-cancer activity is reduced by more than about 50% in a compound with the substituent compared with a compound without the substituent. Examples of suitable substituents include —$R^a$, —OH, —Br, —Cl, —I, —F, —$OR^a$, —O—$COR^a$, —$COR^a$, —CN, —$NO_2$, —COOH, —$SO_3H$, —$NH_2$, —$NHR^a$, —N($R^aR^b$), —$COOR^a$, —CHO, —$CONH_2$, —$CONHR^a$, —CON($R^aR^b$), —$NHCOR^a$, —$NR^cCOR^a$, —$NHCONH_2$, —NH-$CONR^aH$, —NHCON($R^aR^b$), —$NR^cCONH_2$, —$NR^cCON$-$R^aH$, —$NR^cCON(R^aR^b)$, —C(=NH)—$NH_2$, —C(=NH)—$NHR^a$, —C(=NH)—N($R^aR^b$), —C(=$NR^c$)—$NH_2$, —C(=$NR^c$)—$NHR^a$, —C(=$NR^c$)—N($R^aR^b$), —NH—C(=NH)—$NH_2$, —NH—C(=NH)—$NHR^a$, —NH—C(=NH)—N($R^aR^b$), —NH—C(=$NR^c$)—$NH_2$, —NH—C(=$NR^c$)—$NHR^a$, —NH—C(=$NR^c$)—N($R^aR^b$), —$NR^dH$—C(=NH)—$NH_2$, —$NR^d$—C(=NH)—$NHR^a$, —$NR^d$—C(=NH)—N($R^aR^b$), —$NR^d$—C(=$NR^c$)—$NH_2$, —$NR^d$—C(=$NR^c$)—$NHR^a$, —$NR^d$—C(=$NR^c$)—N($R^aR^b$), —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2 R^a$.

$R^a$-$R^d$ are each independently an alkyl group, aromatic group, non-aromatic heterocyclic group or —N($R^aR^b$), taken together, form a substituted or unsubstituted non-aromatic heterocyclic group. The alkyl, aromatic and non-aromatic heterocyclic group represented by $R^a$—$R^d$ and the non-aromatic heterocyclic group represented by —N($R^aR^b$) are each optionally and independently substituted with one or more groups represented by $R^\#$.

$R^\#$ is $R^+$, —O$R^+$, —O(haloalkyl), —S$R^+$, —$NO_2$, —CN, —NCS, —N($R^+$)$_2$, —NHCO$_2R^+$, —NHC(O)$R^+$, —NHNHC(O)$R^+$, —NHC(O)N($R^+$)$_2$, —NHNHC(O)N($R^+$)$_2$, —NHNHCO$_2R^+$, —C(O)C(O)$R^+$, —C(O)CH$_2$C(O)$R^+$, —CO$_2R^+$, —C(O)$R^+$, —C(O)N($R^+$)$_2$, —OC(O)$R^+$, —OC(O)N($R^+$)$_2$, —S(O)$_2R^+$, —SO$_2$N($R^+$)$_2$, —S(O)$R^+$, —NHSO$_2$N($R^+$)$_2$, —NHSO$_2R^+$, —C(=S)N($R^+$)$_2$, or —C(=NH)—N($R^+$)$_2$.

$R^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —$NO_2$, amine, alkylamine or dialkylamine. Optionally, the group —N($R^+$)$_2$ is a non-aromatic heterocyclic group, provided that non-aromatic heterocyclic groups represented by $R^+$ and —N($R^+$)$_2$ that comprise a secondary ring amine are optionally acylated or alkylated.

Preferred substituents for a phenyl group, including phenyl groups represented by $R_1$-$R_4$, include C1-C4 alkyl, C1-C4 alkoxy, C1-C4 haloalkyl, C1-C4 haloalkoxy, phenyl, benzyl, pyridyl, —OH, —$NH_2$, —F, —Cl, —Br, —I, —$NO_2$ or —CN.

Preferred substituents for a cycloalkyl group, including cycloalkyl groups represented by $R_1$ and $R_2$, are alkyl groups, such as a methyl or ethyl group.

Suitable pharmaceutically acceptable carriers may contain inert ingredients which do not inhibit the biological activity of the disclosed disalts. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, Mack Publishing Company, Easton, Pa. Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art (Baker, et al., "Controlled Release of Biological Active Agents", John Wiley and Sons, 1986).

Another embodiment of the present invention is a method of treating a subject with a cancer. Optionally, the method of the invention can be used for a multi-drug resistant cancer as described below. The method comprises the step of administering an effective amount of a reconstituted, lyophilized bis(thio-hydrazide amide) disalt described herein. Preferably, one or more additional anti-cancer drugs are co-administered with the reconstituted, lyophilized bis(thio-hydrazide amide) disalt. Examples of anti-cancer drugs are described below. Preferably, the co-administered anti-cancer drug is an agent that stabilizes microtubules, such as taxol or an analog of taxol.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As noted above, one embodiment of the present invention is directed to treating subjects with a cancer. "Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1(murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B.C. Decker Inc. (2000). The entire teachings of the preceding references are incorporated herein by reference.

In one embodiment, the disclosed method is believed to be particularly effective in treating a subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line); most preferably, this embodiment of the method employs the disodium salt of Compound (1).

The disclosed method is particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

The term "effective amount" and the administration routes are as previously described in U.S. application Ser. No. 11/157,213, the entire contents of which are incorporated herein by reference).

Optionally, the disclosed bis(thio-hydrazide amide) disalts can be co-administered with other anti-cancer agents such as Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentan-thraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides;

insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVAT™ is a humanized anti-CD40L IgG antibody (Biogen); ANTEGREN™ is a humanized anti-VLA-4 IgG antibody (Elan); and CAT-152 is a human anti-TGF-$β_2$ antibody (Cambridge Ab Tech).

Chemotherapeutic agents that can be used in the methods and compositions of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents useful for the treatment or prevention of cancer in the methods and compositions of the invention include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and with the compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

As used herein, a "microtubulin stabilizer" means an anti-cancer agent which acts by arresting cells in the G2-M phases due to stabilization of microtubules. Examples of microtubulin stabilizers include taxol and taxol analogues. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; and analogs and derivatives thereof.

Taxol, also referred to as "Paclitaxel", is a well-known anti-cancer drug which acts by enhancing and stabilizing microtubule formation. Many analogs of taxol are known, including taxotere. Taxotere is also referred to as "Docetaxol". The structures of other taxol analogs are shown in U.S. application Ser. No. 11/157,213 the entire contents of which are incorporated herein by reference. These compounds have the basic taxane skeleton as a common structure feature and have also been shown to have the ability to arrest cells in the G2-M phases due to stabilization of microtubules. Thus, a wide variety of substituents can decorate the taxane skeleton without adversely affecting biological activity. It is also apparent that zero, one or both of the cyclohexane rings of a taxol analog can have a double bond at the indicated positions. For clarity purposes, the basic taxane skeleton is shown below in Structural Formula (VI):

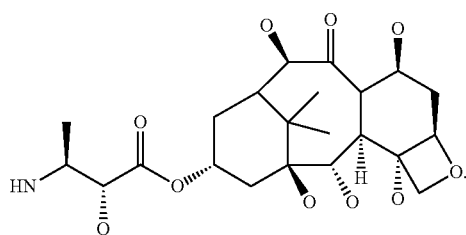

(VI)

Double bonds have been omitted from the cyclohexane rings in the taxane skeleton represented by Structural Formula (VI). The basic taxane skeleton can include zero or one double bond in one or both cyclohexane rings, as indicated in Structural Formulas (VII) and (VIII) below. A number of atoms have also been omitted from Structural Formula (VI) to indicate sites in which structural variation commonly occurs among taxol analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "taxol analog" is defined herein to mean a compound which has the basic taxol skeleton and which promotes microtubule formation. Taxol analogs may be formulated as a nanoparticle colloidal composition to improve the infusion time and to eliminate the need to deliver the drug with Cremophor which causes hypersensitivity reactions in some patients. An example of a taxol analog formulated as a nanoparticle colloidal composition is ABI-007 which is a nanoparticle colloidal composition of protein-stabilized paclitaxel that is reconstituted in saline.

Typically, the taxol analogs used herein are represented by Structural Formula (VII) or (VIII):

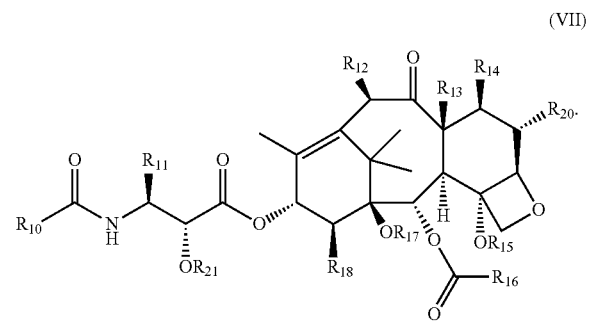

(VII)

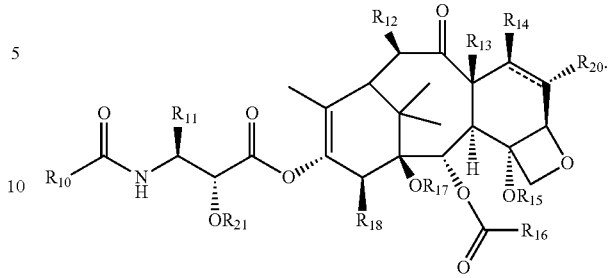

(VIII)

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—$CH_2$—O-(lower alkyl)-S—$CH_2$—O-(lower alkyl).

$R_{13}$ is —H, —$CH_3$, or, taken together with $R_{14}$, —$CH_2$—.

$R_{14}$ is —H, —OH, lower alkoxy, —O—C(O)-(lower alkyl), substituted lower alkoxy, —O—C(O)-(substituted lower alkyl), —O—$CH_2$—O—P(O)(OH)$_2$, —O—$CH_2$—O-(lower alkyl), —O—$CH_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O(substituted lower alkyl), —OC(O)—NH (lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —$CH_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (VII) and (VIII) are defined as follows: $R_{10}$ is phenyl, tert-butoxy, —S—$CH_2$—CH—$(CH_3)_2$, —S—CH$(CH_3)_3$, —S—$(CH_2)_3$ $CH_3$, —O—CH$(CH_3)_3$, —NH—CH$(CH_3)_3$, —CH═C $(CH_3)_2$ or para-chlorophenyl; $R_{11}$ is phenyl, $(CH_3)_2$ CHCH$_2$—, -2-furanyl, cyclopropyl or para-toluoyl; $R_{12}$ is —H, —OH, $CH_3$CO— or —$(CH_2)_2$—N-morpholino; $R_{13}$ is methyl, or, $R_{13}$ and $R_{14}$, taken together, are —$CH_2$—;

$R_{14}$ is —H, —$CH_2$SCH$_3$ or —$CH_2$—O—P(O)(OH)$_2$; $R_{15}$ is $CH_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—$(CH_2)_{13}$—$CH_3$ or —C(O)—$(CH_2)_{14}$—$CH_3$; —C(O)—$CH_2$—CH(OH)—COOH, —C(O)—$CH_2$—O—C (O)—$CH_2$CH(NH$_2$)—CONH$_2$, —C(O)—$CH_2$—O—$CH_2CH_2OCH_3$ or —C(O)—O—C(O)—$CH_2CH_3$.

A taxol analog can also be bonded to or be pendent from a pharmaceutically acceptable polymer, such as a polyacrylamide. One example of a polymer of this type is shown in U.S.

application Ser. No. 11/157,2213. The term "taxol analog", as it is used herein, includes such polymers.

The bis(thio-hydrazide amide) disalts disclosed herein can be prepared by a method of the invention. The method of preparing the disclosed bis(thio-hydrazide amide) disalts includes the steps of combining a neutral bis(thio-hydrazide amide), an organic solvent and a base to form a bis(thio-hydrazide amide) solution; and combining the solution and an organic antisolvent, thereby precipitating a disalt of the bis (thio-hydrazide amide) (e.g., compounds represented by Structural Formulas (I)-(V)). The neutral forms of the disclosed bis(thio-hydrazide amide) disalts can be prepared according to methods described in U.S. Publication Nos. 2003/0045518 and 2003/0119914, both entitled SYNTHESIS OF TAXOL ENHANCERS and also according to methods described in U.S. Publication No. 2004/0225016 A1, entitled TREATMENT FOR CANCERS. The entire teachings of these publications are incorporated herein by reference.

Typically, at least about two molar equivalents of the base are employed for each molar equivalent of neutral bis(thio-hydrazide amide); more typically, from about 2 to about 5 equivalents, or preferably from about 2.0 to about 2.5 equivalents.

Suitable bases can be strong enough to react with a bis (thio-hydrazide amide) to produced a disalt. In various embodiments, the base can be an amine (e.g., triethylamine, diphenylamine, butylamine, or the like); an ammonium hydroxide (e.g., tetramethyammonium hydroxide, tetrabutylammonium hydroxide, or the like); an alkali metal hydroxide (lithium hydroxide, sodium hydroxide, potassium hydroxide, or the like) an alkali metal C1-C6 alkoxide, or an alkali metal amide (e.g., sodium amide, lithium diisopropyl amide, or the like). In some embodiments, the base is sodium hydroxide, potassium hydroxide, sodium C1-C6 alkoxide, potassium C1-C6 alkoxide, sodium amide, or potassium amide, or preferably, sodium hydroxide, sodium methoxide, or sodium ethoxide.

In various embodiments, the base can be an alkali metal hydride (e.g., sodium hydride, potassium hydride, or the like), a divalent metal base (e.g., magnesium oxide) a C1-C6 alkyl alkali metal (e.g., butyllithium), or an aryl alkali metal (e.g., phenyllithium). More typically, the base is lithium hydride, sodium hydride, potassium hydride, butyllithium, butylsodium, butylpotassium, phenyllithium, phenylsodium, or phenylpotassium.

As used herein, an alkali metal includes lithium, sodium, potassium, cesium and rubidium.

The organic solvent can be any organic solvent which is stable when the base is added to a mixture of the bis(thio-hydrazide amide) and the organic solvent. Typically, the organic solvent is polar enough to dissolve the bis(thio-hydrazide amide) salt formed by the method to form a solution. In various embodiments, the organic solvent is water-miscible. The organic solvent can generally be selected from a C1-C4 aliphatic alcohol (e.g., methanol, ethanol, 1-propanol, 2-propanol, or the like), a C1-C4 aliphatic ketone (e.g., acetone, methyl ethyl ketone, 2-butanone, or the like), a C2-C4 aliphatic ether (e.g., diethyl ether, dipropyl ether, diisopropyl ether, or the like), a C2-C4 cycloaliphatic ether (e.g., tetrahydrofuran, dioxane, or the like), dimethyl formamide, dimethyl sulfoxide, N-methylpyrrolidone, a glycol (e.g., ethylene glycol, propylene glycol, tetramethylene glycol, or the like), an alkyl glycol ether (e.g., ethylene glycol dimethyl ether, or the like), and acetonitrile. More typically, the organic solvent can be selected from methanol, ethanol, propanol (e.g., 1-propanol, 2-propanol), butanol (e.g., 1-butanol, tert-butyl alcohol, or the like), acetone, tetrahydrofuran, and methyl ethyl ketone. Preferably, the organic solvent can be selected from methanol, ethanol, acetone, and methyl ethyl ketone.

As used herein, the organic antisolvent is a solvent that when added to the solution created by combining the base, the bis(thio-hydrazide amide) and the organic solvent, causes the bis(thiohydrazide amide) disalt to precipitate out of solution. Typically, the organic antisolvent can be selected from a C5-C10 alkane (e.g., pentane, petroleum ether, hexane, heptane, octane, isooctane, or the like), C5-C10 cycloalkane (e.g., cyclohexane, cyclopentane, or the like), a C3-C10 alkyl ester (e.g., ethyl acetate, propyl acetate, methyl butyrate, or the like, a C3-C10 alkyl ether (e.g., methyl ethyl ether, diethyl ether, methyl propyl ether, or the like), benzene, toluene, and xylene. More typically, the organic antisolvent can be selected from diethyl ether, dipropyl ether (e.g., propyl as 1-propyl or 2-propyl), methyl propyl ether, ethyl propyl ether, methyl tert-butyl ether, methyl acetate, ethyl acetate, propyl acetate, pentane, hexane, cyclohexane, heptane, and petroleum ether. In some embodiments, the organic antisolvent can be a C5-C10 alkane or C5-C10 cycloalkane. In various preferred embodiments, the organic antisolvent can be heptane; or, the organic antisolvent can be diethyl ether or ethyl acetate. In various preferred embodiments, the organic antisolvent can be methyl tert-butyl ether.

In various embodiments, the neutral bis(thio-hydrazide amide) can be substantially insoluble in the organic solvent, thereby forming a mixture, whereby combining the base with the mixture forms a bis(thio-hydrazide amide) solution. Typically, the bis(thio-hydrazide amide) solution can be clear. Generally, between about 0.25 and about 2.5 moles of the neutral bis(thio-hydrazide amide) are combined per each liter of organic solvent, or typically between about 0.75 and about 1.5 moles of the neutral bis(thio-hydrazide amide) are combined per each liter of organic solvent. Preferably, about 1 mole of the neutral bis(thio-hydrazide amide) are combined per each liter of organic solvent.

As used herein, a "bis(thio-hydrazide amide) solution," when formed from the organic solvent, the neutral bis(thio-hydrazide amide), and the base, can include one or more species such as the neutral bis(thio-hydrazide amide), the bis(thio-hydrazide amide) monosalt, the bis(thio-hydrazide amide) disalt, or the like.

In preferred embodiments, the organic solvent is ethanol. Preferably, the base is about 2 molar to about 5 molar aqueous sodium hydroxide, or more preferably from about 2 to about 2.5 molar.

In preferred embodiments, the organic solvent is acetone. Preferably, the base is about 2 molar to about 5 molar ethanolic sodium ethoxide, or more preferably from about 2 to about 2.5 molar.

The bis(thio-hydrazide amide) disalts prepared by the present invention are the disalts disclosed herein, including those represented by Structural Formulas (I)-(V). The neutral bis(thio-hydrazide amides) employed in the disclosed method to prepare the disalts represented by Structural Formulas (I)-(II) can be represented by the following Structural Formulas (I')-(II'), where the variables have the same values and preferred values as in Structural Formulas (I)-(II), respectively:

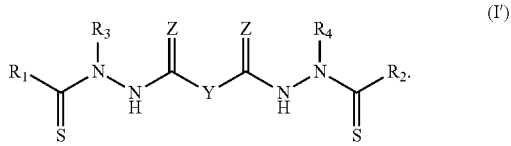

(I')

Thus, as used herein, a neutral bis(thio-hydrazide amide) has at least two hydrogens (e.g., the hydrogens bonded to the nitrogen atoms in Structural Formulas (I') and (II') which can react with the bases described herein to form a disalt.

In Structural Formula (I), $M^+$ is a pharmaceutically acceptable monovalent cation. $M^{2+}$ is a pharmaceutically acceptable divalent cation as described above.

In various preferred embodiments, the organic solvent can be acetone; the base can be ethanolic sodium ethoxide; the organic solvent can be ethanol; the base can be aqueous sodium hydroxide; the antisolvent can be heptane; the neutral bis(thio-hydrazide amide) can be:

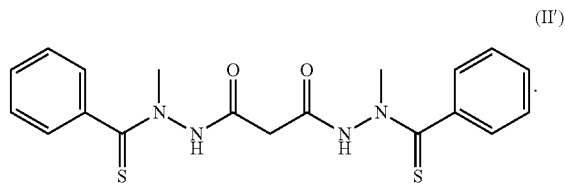 [SMILES: CN(NC(=O)CC(=O)NN(C)C(=S)c1ccccc1)C(=S)c1ccccc1]

(II')

and/or the neutral bis(thio-hydrazide amide) can be:

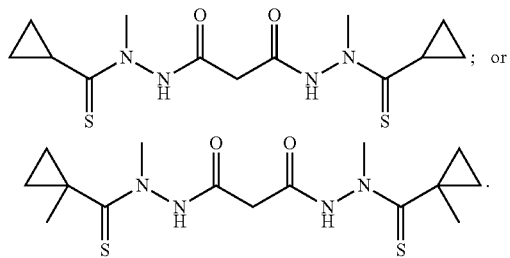

The present invention is illustrated by the following examples, which are not intended to be limiting in any way.

EXEMPLIFICATION

Example 1

Development of Freeze-Drying Parameters

The freeze-dryer shelf was cooled at 0.1° C./min, 0.2° C./min, 0.4° C./min, 1.0° C./min, and by rapidly freezing the vials in a −80° C. freezer. The worst looking cakes were produced when the product was frozen in the −80° C. freezer. This thermal treatment yielded a separated layer at the top of the sample referred to as "flake" throughout this study. Flake formation can be likely explained by a much higher resistance of the upper portion of the cake to a gas flow when compared to the material making up the remainder of the cake. A thinner flake separated from the top of the dried cake when the shelves were cooled at 1° C./min. No flaking was seen using the optimized formulation (as dried using parameters outlined in Table 1) when the shelves were cooled at a rate of 0.1° C./min, 0.2° C./min, or 0.4° C./min. Of note is the fact that other variables were changed when the cooling rate was slowed (e.g., the heating rate during primary drying).

An annealing step was included in order to induce mannitol crystallization and control the size of the crystals. Two annealing temperatures, −8° C. and −20° C., were tested. In addition, the effect of annealing time and number of annealing cycles on the mannitol crystallization and cake appearance were evaluated. The final temperature chosen for annealing was −20° C. Freeze-drying cycles were performed using one or two annealing steps. The cycles utilizing two annealing steps produced a more elegant cake.

Primary drying was performed at shelf temperatures ranging from −10° C. to 10° C. (correlating to product temperatures of −34° C. to −24° C. at the beginning of primary drying). Primary drying at a shelf temperature of −10° C. required a very long drying time (the product temperature was still 12° C. below the shelf temperature after 17 hours). Shelf temperatures above 5° C. during primary drying led to a meltback on the bottom layer of the vial. A shelf temperature of 5° C. was chosen as the final primary drying temperature. In order to prevent heating the sample too quickly, a slow heating ramp from −48° C. to −15° C. at 0.5° C./min, and from −15° C. to 5° C. at 0.1° C./min was introduced. Cake flaking ceased to be a problem in the chosen formulation after the initial cooling rate and the primary drying heating rate were lowered. Additional studies would be necessary to fully differentiate between the effects of these two parameters, but the visual observation of the flake formation just at the beginning of the primary drying cycle when the formulations were cooled more rapidly suggests the importance of the appropriate cooling rate in preventing phase separation of the product.

Secondary drying consisted of a ramp from 5° C. to 45° C., and a holding step at 45° C. 45° C. was chosen because performing secondary drying at that temperature would convert mannitol hydrate into anhydrous mannitol. The final temperature ramp rate chosen was 1° C./min, with the holding step lasting 3 hours.

The recommended freeze-drying cycle chosen for this product is shown in Table 1.

TABLE 1

Recommended freeze-drying cycle.

| Thermal Treatment | | |
|---|---|---|
| Rate (C./min) | Temperature | Hold time (min) |
| 0.0 | −5 | 15 |
| 0.4 | −48 | 60 |
| 1.0 | −20 | 240 |
| 0.5 | −48 | 60 |
| 1.0 | −20 | 180 |
| 0.5 | −48 | 60 |

| Rate (C./min) | Temperature | Pressure (mT) | Hold time (min) |
|---|---|---|---|
| Primary Drying | | | |
| 0.0 | −48 | 150 | 1 |
| 0.5 | −15 | 150 | 0 |
| 0.1 | 5 | 150 | 1500 |
| Secondary Drying | | | |
| 1.0 | 45 | 150 | 180 |

DSC analysis was performed in order to characterize the temperatures of the glass transition of disodium 2-(N'-methyl-N'-thiobenzoyl-hydrazinocarbonyl)-1-(methyl-thiobenzoyl-hydrazono)-ethanolate formulations. The Tg' of approximately −34° C. was detected for a formulation containing 55 mg/ml disodium 2-(N'-methyl-N'-thiobenzoyl-hydrazinocarbonyl)-1-(methyl-thiobenzoyl-hydrazono)-ethanolate and 11% (w/v) mannitol when no annealing step was introduced into a thermal treatment. No Tg' was observed following an annealing step at −8° C. for one hour. The goal of annealing is to crystallize the mannitol in the formulation. The absence of a Tg' (characteristic for amorphous mannitol) in the formulations that underwent an annealing step demonstrated that the annealing was sufficient for mannitol crystallization.

DSC analysis was also performed for the freeze-dried samples in order to determine the Tg' and confirm the absence of mannitol hydrate. The concentration of mannitol hydrate can be estimated based on its characteristic endothermic melting at 80° C. The Tg' of the freeze-dried disodium 2-(N'-methyl-N'-thiobenzoyl-hydrazinocarbonyl)-1-(methyl-thiobenzoyl-hydrazono)-ethanolate-mannitol formulation was approximately 56° C. No mannitol hydrate melts were observed in the dried product, indicating that the secondary drying step was sufficient in converting the metastable mannitol hydrate to an anhydrous form of mannitol. Also, no crystallization exotherms were detected in the thermal scans, showing that the mannitol crystallized during the freezing and annealing processes.

In freeze-dried products, 1% (w/w) residual moisture is considered to be a characteristic for completely dried product. In order to estimate the secondary drying time required to obtain a product with the moisture level below 1% the formulations were pulled out from freeze-drier during different timepoints of secondary drying using sample thief. The secondary drying step of the final cycle (a 45° C. shelf temperature for 3 hours) was adequate for achieving a dry product. The final freeze-drying cycle chosen for this study produced a product with 0.9% residual moisture.

The stability of disodium 2-(N'-methyl-N'-thiobenzoyl-hydrazinocarbonyl)-1-(methyl-thiobenzoyl-hydrazono)-ethanolate during freeze-drying was evaluated via reverse-phase HPLC analysis. Disodium 2-(N'-methyl-N'-thiobenzoyl-hydrazinocarbonyl)-1-(methyl-thiobenzoyl-hydrazono)-ethanolate proved to be stable through all of the freeze-drying cycles tested, as no degradation products were detected. On average, main peak purity of 97% was observed for disodium 2-(N'-methyl-N'-thiobenzoyl-hydrazinocarbonyl)-1-(methyl-thiobenzoyl-hydrazono)-ethanolate than the cake body.

The flakes that were produced in many of the freeze-drying runs were tested for potency, and compared to the cake body. Equal weights of both were reconstituted in the same volume of deionized water. This analysis indicated that the flake contains a higher concentration of disodium 2-(N'-methyl-N'-thiobenzoyl-hydrazinocarbonyl)-1-(methyl-thiobenzoyl-hydrazono)-ethanolate than the cake body. This could be due to a slight phase separation during freezing. The separation does not appear to affect the stability of the product.

RP-HPLC analysis showed that the freeze-drying process used in this study did not adversely affect the stability of disodium 2-(N'-methyl-N'-thiobenzoyl-hydrazinocarbonyl)-1-(methyl-thiobenzoyl-hydrazono)-ethanolate.

The osmolality of the freeze-dried product (55.5 mg/mL disodium 2-(N'-methyl-N'-thiobenzoyl-hydrazinocarbonyl)-1-(methyl-thiobenzoyl-hydrazono)-ethanolate and 11% mannitol) was assessed following reconstitution in water for injection (WFI), 0.9% (w/v) NaCl in WFI, or 5% (w/v) dextrose in WFI. The osmolality following reconstitution with 10 mL of solvent, as well as after dilution to 150 mL was measured. After dilution to 150 mL with either the NaCl or dextrose solutions, the product is in the range of isotonicity.

Example 2

Freeze Drying of disodium 2-(N'-methyl-N'-thiobenzoyl-hydrazinocarbonyl)-1-(methyl-thiobenzoyl-hydrazono)-ethanolate and Choice of Excipients, Fill Volumes and Vial Size Freeze-drying was performed in a Genesis 25EL freeze-dryer (Virtis). Sample vials were placed directly on the shelf. Space leftover on the shelf was filled with empty vials. The vial headspace was filled with air.

Tg' and Tg were evaluated using a PYRIS Diamond DSC. Samples for Tg' determination were prepared by loading 50 µL of sample into a 500 µL aluminum pan, then sealing the pan using the sealing press. The thermal program used to identify Tg' (without annealing) was:
1. Ramp from 20° C. to −50° C. at 10° C./min
2. Hold at −50° C. for 4 minutes
3. Ramp from −50° C. to 20° C. at 10° C./min
The thermal program used to identify Tg' that included an annealing step was:
1. Ramp from 20° C. to −45° C. at 10° C./min
2. Hold at −45° C. for 10 minutes
3. Ramp from −45° C. to −8° C. at 10° C./min
4. Hold at −8° C. for 1 hour
5. Ramp from −8° C. to −70° C. at 10° C./min
6. Hold at −70° C. for 5 minutes
7. Ramp from −70° C. to 20° C. at 10° C./min
Tg' was taken to be the midpoint of the transition.

Freeze-dried samples used in the determination of Tg' were prepared by weighing out a few milligrams of sample into a 50 µL aluminum pan and sealing it. The thermal program used to determine Tg' ramped the temperature from 25° C. to 150° C. at 10° C./min.

Residual moisture was analyzed using the Karl Fisher. The dried samples were reconstituted with methanol. The vials containing samples were weighed. The sample was injected into the coulometer, and the water content was measured. The sample vial was then weighed to determine the amount of sample added to the coulometer. The percentage of water in the sample could then be determined.

Reverse phase HPLC was used to quantify the potency and purity of; disodium 2-(N'-methyl-N'-thiobenzoyl-hydrazinocarbonyl)-1-(methyl-thiobenzoyl-hydrazono)-ethanolate following freeze-drying. The analysis was performed as detailed in the analytical method.

Osmolality of a formulation containing 55.5 mg/mL; disodium 2-(N'-methyl-N'-thiobenzoyl-hydrazinocarbonyl)-1-(methyl-thiobenzoyl-hydrazono)-ethanolate and 11% (w/v) mannitol was tested after reconstitution in water for injection (WFI), 0.9% NaCl in WFI, or 5% dextrose in WFI. An Osmette XL was used to measure the osmolality after reconstitution in 10 mL of solvent as well as after dilution to 150 mL. Osmolality measurements were also made of the solvents.

The crystalline bulking agents that were explored for use in the freeze-dried formulation were mannitol and glycine. Formulations containing 55.5 mg/mL and either 1:1, 2.5:1, 4:1, or 5:1 molar ratios of mannitol:disodium 2-(N'-methyl-N'-thiobenzoyl-hydrazinocarbonyl)-1-(methyl-thiobenzoyl-hydrazono)-ethanolate or 0.5:1, 1:1, or 2.5:1 molar ratios of glycine:disodium 2-(N'-methyl-N'-thiobenzoyl-hydrazinocarbonyl)-1-(methyl-thiobenzoyl-hydrazono)-ethanolate were used in the initial formulation development experiments.

Formulations with 1:1 and 2.5:1 mannitol:disodium 2-(N'-methyl-N'-thiobenzoyl-hydrazinocarbonyl)-1-(methyl-thiobenzoyl-hydrazono)-ethanolate resulted in phase separation and some collapse upon freeze-drying. While both 4:1 and 5:1 mannitol:disodium 2-(N'-methyl-N'-thiobenzoyl-hydrazinocarbonyl)-1-(methyl-thiobenzoyl-hydrazono)-ethanolate formulations produced rugged cakes, the 5:1 formulation formed the more pharmaceutically elegant cake. A very thin flake did separate from the tops of the cakes in these two formulations.

For the glycine containing formulations, the 0.5:1 glycine:disodium 2-(N'-methyl-N'-thiobenzoyl-hydrazinocarbonyl)-1-(methyl-thiobenzoyl-hydrazono)-ethanolate samples displayed significant shrinkage and some collapse. The 2.5:1 glycine:disodium 2-(N'-methyl-N'-thiobenzoyl-hydrazinocarbonyl)-1-(methyl-thiobenzoyl-hydrazono)-ethanolate formulations produced elegant cakes but did not reconstitute completely. Although 1:1 glycine:disodium 2-(N'-methyl-N'-thiobenzoyl-hydrazinocarbonyl)-1-(methyl-thiobenzoyl-hydrazono)-ethanolate samples produced elegant cakes on first appearance, vigorous shaking reduced them to a powder.

Based on these results, mannitol was selected for further development studies. The 5:1 mannitol:disodium 2-(N'-methyl-N'-thiobenzoyl-hydrazinocarbonyl)-1-(methyl-thiobenzoyl-hydrazono)-ethanolate formulation equated to an 11% (w/v) mannitol solution for 55 mg/mL disodium 2-(N'-methyl-N'-thiobenzoyl-hydrazinocarbonyl)-1-(methyl-thiobenzoyl-hydrazono)-ethanolate solution, and this was used as the starting point for the next round of formulation studies.

Using an 11% (w/v) mannitol solution, the concentration of disodium 2-(N'-methyl-N'-thiobenzoyl-hydrazinocarbonyl)-1-(methyl-thiobenzoyl-hydrazono)-ethanolate was varied at 42 mg/mL, 55.5 mg/mL, and 83 mg/mL in order to test the effects of disodium 2-(N'-methyl-N'-thiobenzoyl-hydrazinocarbonyl)-1-(methyl-thiobenzoyl-hydrazono)-ethanolate concentration on the properties of freeze-dried cake. All of the formulations produced pharmaceutically elegant cakes with a thin flake separating from the top in most cases. The reconstitution time of the 83 mg/mL formulation was almost 3 minutes, which is undesirably long. The other formulations reconstituted in about 20 seconds. A formulation with 67 mg/mL disodium 2-(N'-methyl-N'-thiobenzoyl-hydrazinocarbonyl)-1-(methyl-thiobenzoyl-hydrazono)-ethanolate with 11% mannitol of was also evaluated, and produced an elegant cake that reconstituted in about 20 seconds.

After narrowing down the type and concentrations of excipients and disodium 2-(N'-methyl-N'-thiobenzoyl-hydrazinocarbonyl)-1-(methyl-thiobenzoyl-hydrazono)-ethanolate, a more focused study, varying mannitol and disodium 2-(N'-methyl-N'-thiobenzoyl-hydrazinocarbonyl)-1-(methyl-thiobenzoyl-hydrazono)-ethanolate concentrations over a smaller range was performed. The main goal of this study was to determine the concentrations of mannitol and disodium 2-(N'-methyl-N'-thiobenzoyl-hydrazinocarbonyl)-1-(methyl-thiobenzoyl-hydrazono)-ethanolate that would create the most pharmaceutically elegant cake. The vial size was also varied in these studies, using 20 mL and 50 mL lyophilization vials. The formulations used in this study are listed in Table 2.

TABLE 2

Formulations used in formulation study.

| Formulation # | Conc. disodium 2-(N'-methyl-N'-thiobenzoyl-hydrazinocarbonyl)-1-(methyl-thiobenzoyl-hydrazono)-ethanolate (mg/mL) | Conc. Mannitol (% w/v) | Vial sizes used (mL) |
|---|---|---|---|
| 1 | 67.6 | 11 | 20 and 50 |
| 2 | 56.2 | 11 | 20 and 50 |
| 3 | 44.8 | 11 | 50 |
| 4 | 33.8 | 11 | 50 |
| 5 | 27.0 | 11 | 50 |
| 6 | 57.1 | 14 | 20 and 50 |
| 7 | 45.6 | 14 | 50 |
| 8 | 34.8 | 6 | 50 |
| 9 | 27.9 | 6 | 50 |
| 10 | 67.6 | 14 | 20 and 50 |

Formulations 8 and 9 turned to a powder upon shaking. Formulations 4 and 5 failed to produce rugged cakes. The other formulations did produce rugged cakes. Flaking was present in many of the vials, but formulations 1 and 6 showed less flaking than the other formulations.

Further studies were performed using formulations 1, 2, 6, and a formulation with 67 mg/ml disodium 2-(N'-methyl-N'-thiobenzoyl-hydrazinocarbonyl)-1-(methyl-thiobenzoyl-hydrazono)-ethanolate and 14% mannitol (formulation 10) with a freeze-drying cycle as outlined in Table 1 in an attempt to minimize flaking. Both formulations 1 and 2 resulted in pharmaceutically acceptable cake that did not exhibit any flaking, however formulation 2 produced the more elegant cake.

The results of the formulation work performed on this project resulted in an optimal freeze-dried (as outlined in Table 1) disodium 2-(N'-methyl-N'-thiobenzoyl-hydrazinocarbonyl)-1-(methyl-thiobenzoyl-hydrazono)-ethanolate formulation consisting of 55.5 mg/mL disodium 2-(N'-methyl-N'-thiobenzoyl-hydrazinocarbonyl)-1-(methyl-thiobenzoyl-hydrazono)-ethanolate with 11% (w/v) mannitol in water for injection. The pH for this formulation is around 10.9. This formulation, along with a optimized freeze-drying cycle as outlined in Table 1 will result in a rugged and pharmaceutically elegant product. By filling 20 mL vials with 12 mL of 55.5 mg/mL disodium 2-(N'-methyl-N'-thiobenzoyl-hydrazinocarbonyl)-1-(methyl-thiobenzoyl-hydrazono)-ethanolate, the desired dose of 670 mg disodium 2-(N'-methyl-N'-thiobenzoyl-hydrazinocarbonyl)-1-(methyl-thiobenzoyl-hydrazono)-ethanolate can be delivered in a single vial which provides additional economical advantage to this formulation.

Example 3

In a glass beaker 160 g of purified water was heated to approximately 65° C. 9.06 g of hydroxyethyl starch (HES) was slowly added to the water and mixed. Mixing was continued until the HES dissolved (less than 10 minutes). The solution was cooled to room temperature and then 11.70 g of disodium 2-(N'-methyl-N'-thiobenzoyl-hydrazinocarbonyl)-1-(methyl-thiobenzoyl-hydrazono)-ethanolate was added. This was mixed until all the disodium 2-(N'-methyl-N'-thiobenzoyl-hydrazinocarbonyl)-1-(methyl-thiobenzoyl-hydrazono)-ethanolate was in solution (less than 10 minutes). All the solution was quantitatively transferred to a 200 mL volumetric flask and diluted to 200 mL with purified water. The final unit formulation was 55.5 mg/ml STA-4783 sodium and 45 mg/ml HES.

8.0 mL of the solution was filled into 20 mL Type I glass vials. Freeze-dry stoppers were placed on the filled vials, which were then loaded into the freeze-dryer. The freeze-drying cycle was as follows in Table 3:

TABLE 3

| Stage | Shelf Set Point Temperature (° C.) | Time (hours) |
|---|---|---|
| Freezing | 5 to −40 | 1.8 |
| Hold | −40 | 3 |
| Ramp | −40 to −25 | 0.3 |
| Primary Drying | −25 (100 mtorr) | 48 |
| Ramp | −25 to 25 | 8 |
| Secondary Drying | 25 (100 mtorr) | 12 |

The appearance and reconstitution times of the resulting freeze-dried cakes were evaluated.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising a compound represented by the following structural formula:

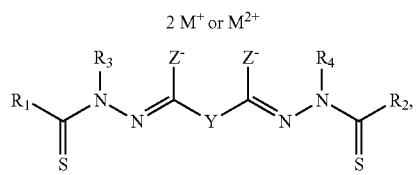

wherein:
Y is a covalent bond or a substituted or unsubstituted straight chained hydrocarbyl group;
$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;
Z is —O or —S; and
$M^+$ is a pharmaceutically acceptable monovalent cation and $M^{2+}$ is a pharmaceutically acceptable divalent cation; and
a pharmaceutically acceptable excipient selected from hydroxyethyl starch, dextran and combinations thereof, and
wherein the molar ratio of said compound to said excipient is from 1:20 to 1:1.

2. The composition of claim 1, wherein the compound is represented by the following structural formula:

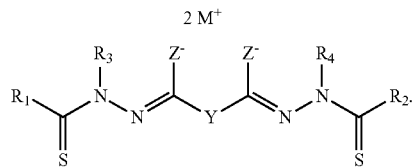

3. The composition of claim 2, wherein the pharmaceutically acceptable cation is $Na^+$ or $K^+$.

4. The composition of claim 1, wherein Z is O; $R_1$ and $R_2$ are the same; and $R_3$ and $R_4$ are the same.

5. The composition of claim 4, wherein:
Y is a covalent bond, —C($R_5R_6$)—, —($CH_2CH_2$)—, trans-(CH=CH)—, cis-(CH=CH)— or —(CC)— group; and
$R_5$ and $R_6$ are each independently —H, an aliphatic or substituted aliphatic group, or $R_5$ is —H and $R_6$ is a substituted or unsubstituted aryl group, or $R_5$ and $R_6$, taken together, are a C2-C6 a substituted or unsubstituted alkylene group.

6. The composition of claim 5, wherein:
Y is —C($R_5R_6$)—;
$R_1$ and $R_2$ are each a substituted or unsubstituted aryl group; and
$R_3$ and $R_4$ are each a substituted or unsubstituted aliphatic group.

7. The composition of claim 6, wherein $R_1$ and $R_2$ are each an optionally substituted phenyl group.

8. The composition of claim 7, wherein $R_1$ and $R_2$ are each a substituted phenyl group, and said phenyl group is substituted with C1-C4 alkyl, C1-C4 alkoxy, C1-C4 haloalkyl, C1—C4 haloalkoxy, phenyl, benzyl, pyridyl, —OH, —$NH_2$, —F, —Cl, —Br, —I, —$NO_2$ or —CN.

9. The composition of claim 5, wherein
Y is —$CR_5R_6$—;
$R_1$ and $R_2$ are both a substituted or unsubstituted aliphatic group;
$R_5$ is —H; and
$R_6$ is —H or a substituted or unsubstituted aliphatic group.

10. The composition of claim 1, wherein the composition is a lyophilizate.

11. The composition of claim 10, wherein the molar ratio of said compound to said excipient is from 1:10 to 1:1.

12. The composition of claim 10, wherein the molar ratio of said compound to said excipient is 1:5.5 to 1:2.0.

13. The composition of claim 10, wherein the excipient is hydroxyethyl starch.

14. The composition of claim 10, wherein the excipient is dextran.

15. The composition of claim 13, wherein the composition is an annealed composition.

16. The composition of claim 1, wherein the compound is represented by the following structural formula:

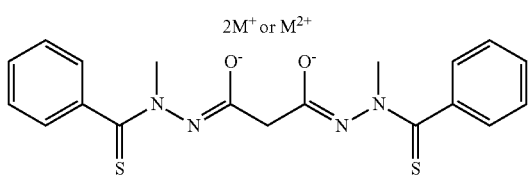

wherein:
$M^+$ is a pharmaceutically acceptable monovalent cation and $M^{2+}$ is a pharmaceutically acceptable divalent cation.

17. The composition of claim 16, wherein the compound is represented by the following structural formula:

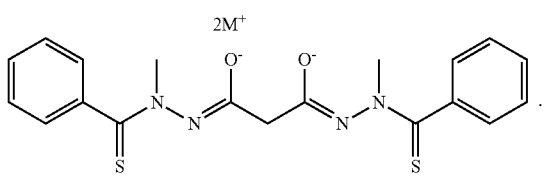 [SMILES: CN(/N=C(\[O-])C/C([O-])=N/N(C)C(=S)c1ccccc1)C(=S)c1ccccc1]

18. The composition of claim 17, wherein the pharmaceutically acceptable cation is Na⁺ or K⁺.

19. The composition of claim 15, wherein the compound is represented by the following structural formula:

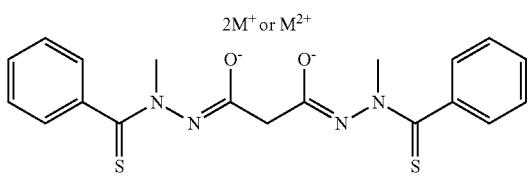

wherein:
M⁺ is a pharmaceutically acceptable monovalent cation and $M^{2+}$ is a pharmaceutically acceptable divalent cation.

20. The composition of claim 19, wherein the compound is represented by the following structural formula:

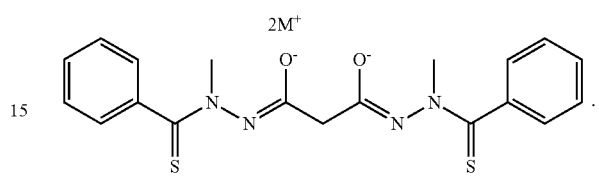

21. The composition of claim 20, wherein the pharmaceutically acceptable cation is Na⁺ or K⁺.

\* \* \* \* \*